United States Patent [19]

Chiou

[11] Patent Number: 4,459,309

[45] Date of Patent: Jul. 10, 1984

[54] COMPOSITIONS AND METHODS OF LOWERING INTRAOCULAR PRESSURE IN THE HYPERTENSIVE MAMMALIAN EYE

[75] Inventor: George C. Y. Chiou, College Station, Tex.

[73] Assignee: The Texas A&M University System, College Station, Tex.

[21] Appl. No.: 340,529

[22] PCT Filed: May 5, 1980

[86] PCT No.: PCT/US80/00515

§ 371 Date: Dec. 18, 1981

§ 102(e) Date: Dec. 18, 1981

[87] PCT Pub. No.: WO81/03123

PCT Pub. Date: Nov. 12, 1981

[51] Int. Cl.³ .............................................. A61K 31/27
[52] U.S. Cl. ..................................................... 424/300
[58] Field of Search ......................................... 424/300

[56] References Cited

PUBLICATIONS

J. Pharm. Sci., 69, (3), 332-334, (1980), Trzeciakowski et al.
J. Pharm. Sci., 67, (4), 531-535, (1978), Trzeciakowski et al.
Chem. Abst., 93, 422j, (1980), Trzeciakowski et al.
AMA-Drug Evaluation, 2nd ed., (1973), Chapter 69, p. 680.

*Primary Examiner*—Douglas W. Robinson
*Attorney, Agent, or Firm*—Vorys, Sater, Seymour & Pease

[57] ABSTRACT

Compositions for treating open-angle glaucoma comprising N,N-dimethylaminoethyl carbamate and method of treating ocular hypertension by topically administering such compound to the hypertensive eye.

10 Claims, 5 Drawing Figures

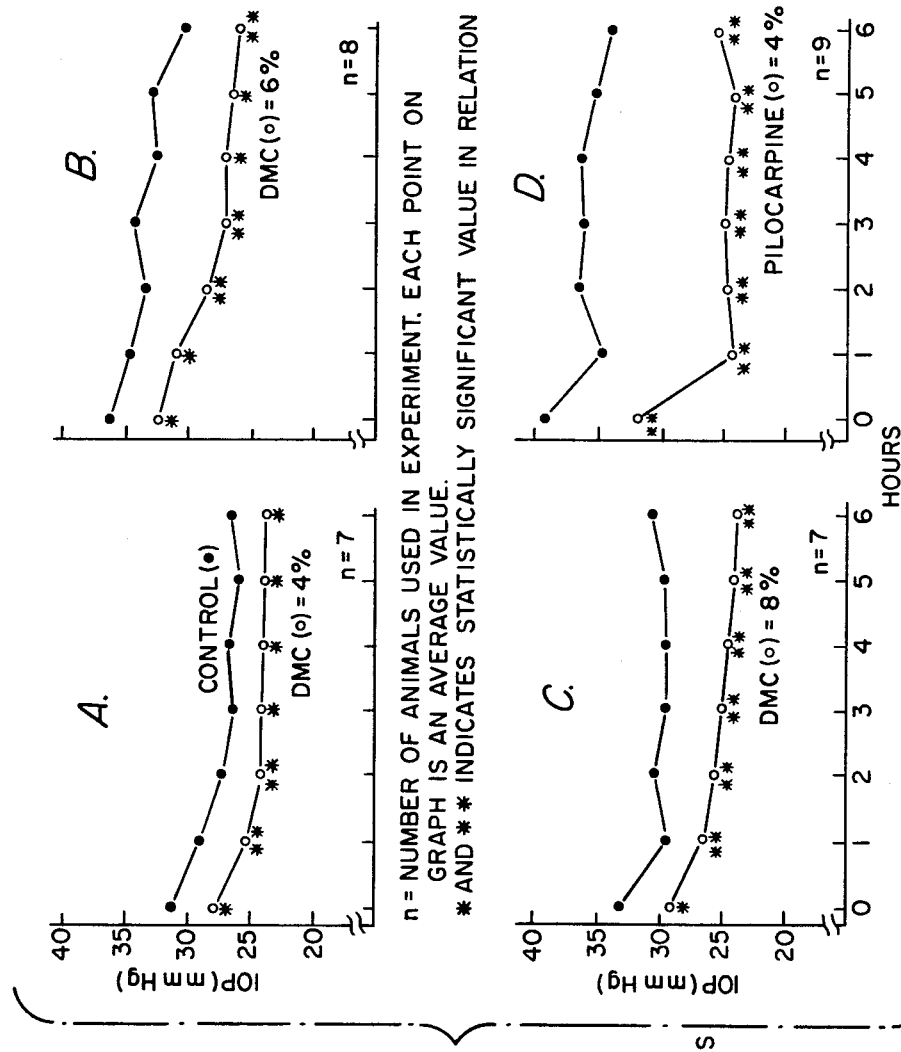

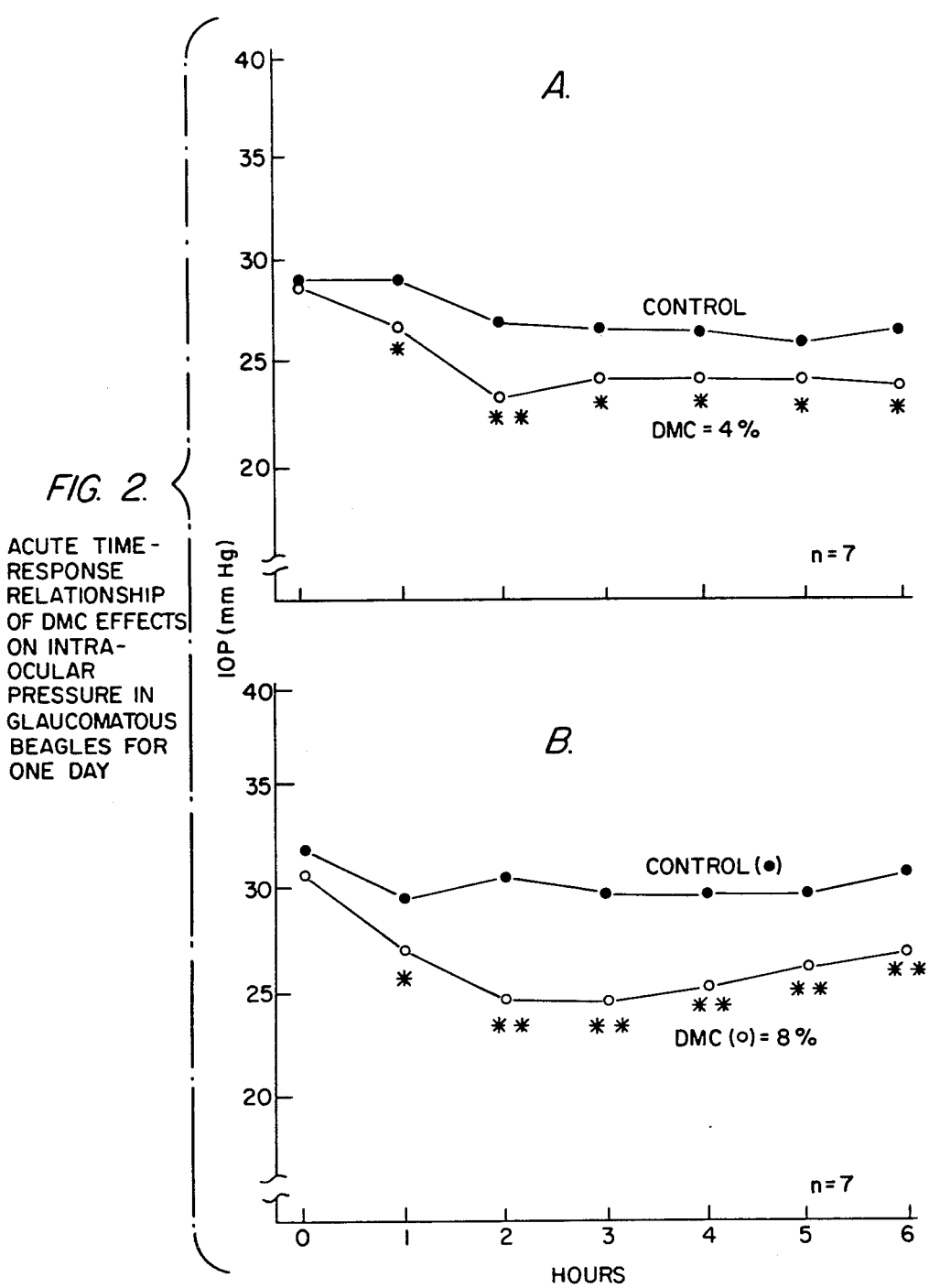

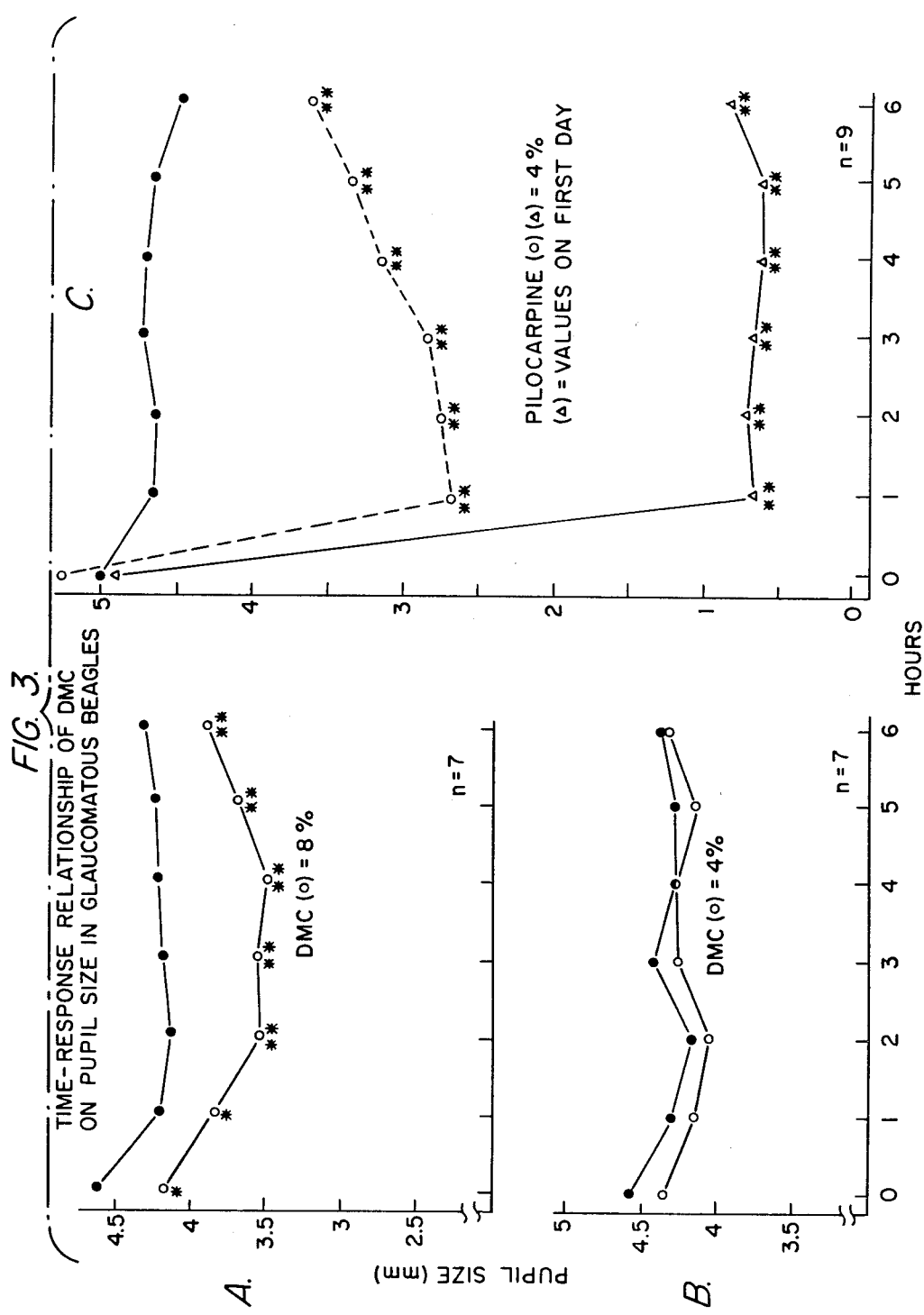

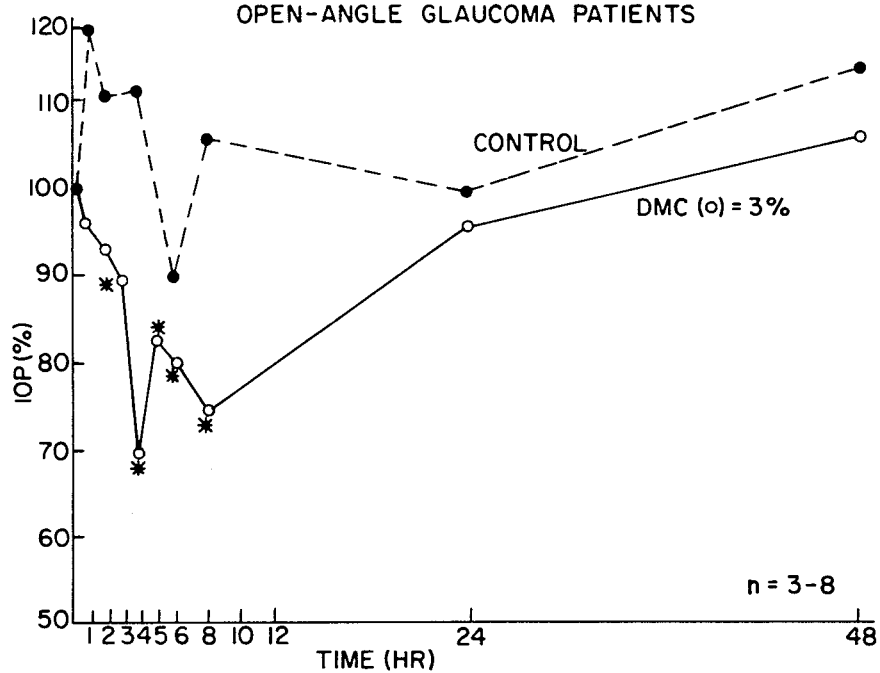
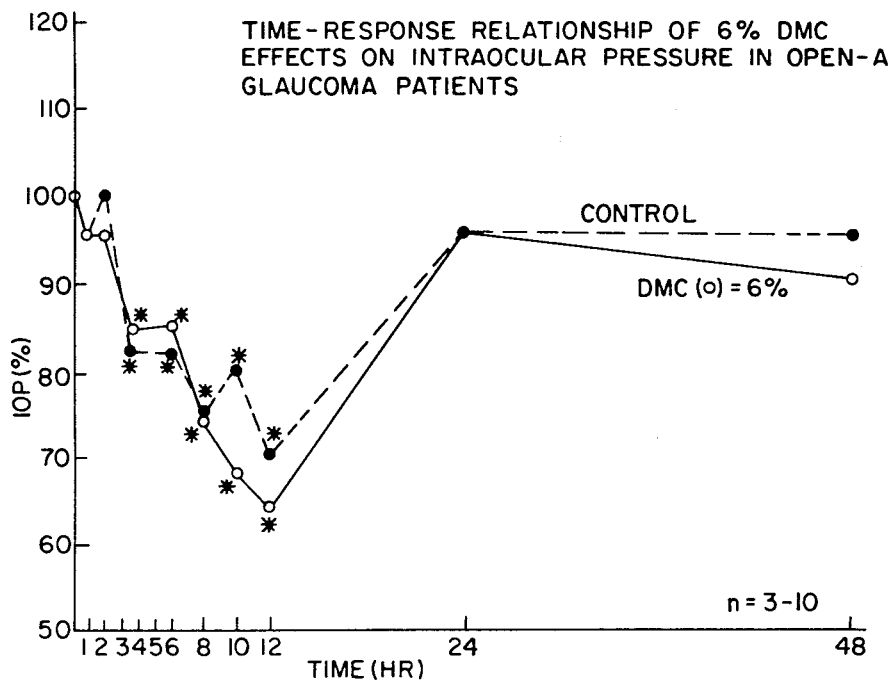

COMPOSITIONS AND METHODS OF LOWERING INTRAOCULAR PRESSURE IN THE HYPERTENSIVE MAMMALIAN EYE

The invention described herein was made in the course of work under a grant or award from the Department of Health, Education, and Welfare.

BACKGROUND OF THE INVENTION

This invention relates to a method of treating glaucoma and ocular hypertension in mammals. More particularly, this invention involves a method of lowering intraocular pressure in the mammalian eye by topically applying thereto an ophthalmologically acceptable, effective amount for lowering intraocular pressure of N,N-dimethylaminoethyl carbamate ("N-demethylated carbachol"). The invention further relates to ophthalmic compositions comprising this compound as an active ingredient.

Ocular hypertension is associated with glaucoma, a disease of the eye which is characterized by a progressive increase in intraocular pressure. If the eye is left untreated, such increased pressure will damage the optic nerve head resulting in a corresponding loss of visual field and, ultimately, blindness. Accordingly, a common treatment for glaucoma is the administration to the diseased eye of a substance which is effective in lowering such intraocular pressure.

Basically, there are two types of drugs available for this purpose. One reduces aqueous humor formation and the other increases aqueous humor outflow to reduce the intraocular pressure. Among all of these drugs, pilocarpine, which belongs to the latter type, is the most widely used drug and has been in use for more than a century. Although effective for its intended purpose, when used in the eye pilocarpine and similar drugs produce many unwanted side effects, including local irritation, tearing, burning sensation, ciliary spasm, miosis, and headache. These side effects are thought to be due to two major reasons: (1) instability of the drug at high PH medium necessitating the formulation of pilocarpine-containing ophthalmic solutions at a pH as low as 4.5 to 5.5, and (2) the chemical structure of pilocarpine is entirely different from the natural cholinergic neurotransmitter, acetylcholine, a factor which could produce the sypmtoms of tearing, headache, etc.

It has now been found, according to this invention that intraocular pressure can be reduced in hypertensive eyes without the unwanted side effects commonly associated with pilocarpine and similar drugs.

SUMMARY OF THE INVENTION

Methods are provided for treating open-angle glaucoma by reducing the intraocular pressure in the hypertensive mammalian eye which comprise topically applying to such eye an ophthalmologically acceptable, effective amount for lowering intraocular pressure of a cholinergically active tertiary nitrogen derivative of choline which is capable of being solubilized in aqueous solution and remains stable and active at pH within the range of about 5.5 to about 8.0. In particular, there is provided a method of reducing intraocular pressure in mammals having intraocular hypertension comprising topically administering to a hypertensive eye an opthalmologically acceptable, effective amount for lowering intraocular pressure of a compound selected from N,N-dimethylaminoethyl carbamate (N-demethylated carbachol) and ophthalmologically acceptable acid addition salts thereof. Pharmaceutical compositions comprising an acid addition salt of N-demethylated carbachol and a non-toxic, pharmaceutically acceptable, ophthalmological carrier are particularly suitable for use in accordance with this invention. In a preferred form, such compositions will comprise ophthalmic solutions or ointments, but other known ocular drug delivery means such as, for example, lamella (e.g. a drug containing, water-soluble gel of glycerinated gelatin), polymer inserts, or soft contact lens are also included within the scope of the invention.

BRIEF DESCRIPTION OF DRAWINGS

In the drawings, which are set forth to illustrate the embodiments described in the examples, the figures are as follows:

FIG. 1 is a graph illustrating the time-response relationship of N-demethylated carbachol and pilocarpine effects, respectively, on intraocular pressure in glaucomatous beagles for five days.

FIG. 2 is a graph showing the acute time-response relationship of N-demethylated carbachol effects on intraocular pressure in glaucomatous beagles for one day.

FIG. 3 is a graph illustrating the time-response relationship of N-demethylated carbachol and pilocarpine effects, respectively, on pupil size in glaucomatous beagles.

FIG. 4 is a graph depicting the time-response relationship of 3% N-demethylated carbachol effects on intraocular pressure in open-angle glaucoma patients.

FIG. 5 is a graph demonstrating the time-response relationship of 6% N-demethylated carbachol effects on intraocular pressure in open-angle glaucoma patients.

DETAILED DESCRIPTION OF THE INVENTION

In accordance with the practice of this invention, a novel anti-glaucoma composition is provided which when topically administered to the hypertensive mammalian eye will reduce intraocular pressure in that eye without causing the unwanted side effects which are characteristic of drugs previously used for this purpose.

The invention is based on the discovery that N,N-dimethylaminoethyl carbamate (N-demethylated carbachol) and like cholinergically active compounds which are chemically related to choline but which have a tertiary, as opposed to quaternary, nitrogen moiety in their structures, are effective in decreasing intraocular pressure when topically administered to the eye. The compound N,N-dimethylaminoethyl carbamate, as such, is known but its use in the treatment of open-angle glaucoma has not been clearly established previously. The compound is represented by the following formula:

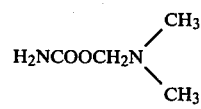

and may be prepared according to the method of Hazard et. al. (BUL. SOC. CHIM. FR., (1961) 2087) which, in essence, comprises the catalyzed reaction of dimethylaminoethanol with an excess of ethylacarbamate in toluene. Of course, as will be appreciated, this compound may also be considered as the compound carbachol which has been "demethylated" to remove the quaternary charge. Accordingly, suitable methods of dealkylation may also be employed to prepare the tertiary nitrogen derivative contemplated by the present invention. Hereafter, the term "N-demethylated carbachol" should be understood to include the tertiary nitrogen compound either synthesized directly or formed by demethylation techniques.

According to the invention, the compounds are preferably administered in the form of an ophthalmic pharmaceutical composition adapted for topical administration to the eye, such as solutions or ointments, but it may also be incorporated in other known ocular drug delivery means such as lamella, polymeric inserts, or hydrophilic contact lenses.

When used in accordance with this invention, N-demethylated carbachol will usually be employed in the form of an ophthalmologically acceptable, acid addition salt. Such as expression, as used herein, is intended to define those salts and compositions which are substantially non-toxic or non-irritating upon topical application to the eye, and otherwise prepared in accord with the requirements, practicalities and good pharmaceutical practices associated with ophthalmic products. By way of example, such acid addition salts may be those derived from organic or inorganic acids which are non-irritating to the eye such as hydrochloric, hydrobromic, sulphuric, phosphoric, methanesulfonic, acetic, citric, malic, succinic, lactic, tartaric, benzoic, and the like. In practicing the method of the present invention, the hydrochloride salt is particularly preferred.

Formulations including the preferred compound of the invention have been found to be effective if they contain from about 3% to about 9% by weight of the N-demethylated carbachol. Higher dosages, for example about 12%, or even higher are still effective and may be found necessary for some glacomatous patients, but the concern here should be that too strong a dose may suppress intraocular pressure to below normal levels. Lower dosages can also be employed provided the dose is effective in lowering intraocular pressure.

In a preferred embodiment, a unit dosage form will contain about 4.5 mgs. to about 9 mgs. of N-demethylated carbachol hydrochloride. When applied to the hypertensive mammalian eye in solution form, such an effective dosage will generally require 1 to 2 drops.

According to this invention, pharmaceutical preparations containing N-demethylated carbachol as active ingredient may be conveniently prepared by admixing the active ingredient with a non-toxic, pharmaceutically acceptable, organic, or inorganic carrier. Typical of such pharmaceutically acceptable carriers are, for example, water, mixtures of water and water miscible solvents such as the lower alkanols or aralkanols, vegetable oils, polyalkylene glycols, petroleum based jelly, ethylcellulose, ethyloleate, carboxymethylcellulose, polyvinylpyrrolidone, isopropyl myristate, and other conventionally employed pharmaceutically acceptable carriers. The pharmaceutically preparation may also contain non-toxic auxiliary substances such as emulsifying, preserving, wetting, or bodying agents and the like.

Aqueous ophthalmic solutions used in accordance with this invention may be formulated, for example, in accordance with the procedures set forth in Chapter 83 of Remington's Pharmaceutical Sciences, 14th Edition, Mack Publishing Company. Such ophthalmic solutions are sterile and may contain a bacteriological preservative to maintain sterility during use. The quaternary ammonium bacteriostats such as benzalkonium chloride are satisfactory for this purpose. An antioxidant may also be employed if desired. By way of example, suitable antioxidents include sodium bisulfite, N-acetylcysteine salts, sodium ascorbate and other water soluble ophthalmologically acceptable antioxidants known to the pharmaceutical art. Particularly improtant in contrasting the prior art use of pilocarpine is the fact that solutions according to the present invention may be buffered to a pH of between 5.5 to 8.0, and especially 7-8, without any adverse effect on the efficacy or stability of the active ingredient. Suitable for this purpose are water-soluble buffering agents such as alkali, alkali earth carbonates, phosphates, bicarbonates, citrates, borates and the like.

Ointments employed in practicing the present invention may be prepared utilizing known pharmaceutical techniques with conventional vehicles.

In accord with this invention, ocular inserts may be placed so that they are retained in contact with the surface of the eye and diffuse an effective, intraocular pressure lowering dose of N-demethylated carbachol to the eye over a prolonged period of time.

The following examples are given by way of illustration.

EXAMPLE 1

The following illustrates the efficacy of N-demethylated carbachol hydrochloride (DMC) in reducing intraocular pressure of spontaneously developed glaucomatous beagle dogs.

Two drops of 0.4% benoxinate (Dorsacaine, Dorsey Laboratories) were instilled in each eye prior to pressure determination. The intraocular pressure was measured with the Mackay-Marg electronic applanation tonometer (Berkeley Bio-Engineering, San Leandro, Calif.). Pupil size was measured with calipers under uniform artificial illumination. Baseline values of intraocular pressure and pupil size were determined for three successive days followed by drug treatment for five consecutive days. For drug treatment, 50 $\mu$l of sterile buffered (pH 7.4) solution of DMC was administered randomly to one eye of each animal; the other eye received 50 $\mu$l of saline as a control. Intraocular pressure and pupil size were recorded hourly for 6 hours after drug instillation and compared with baseline values. "Paired" t-test was performed for statistical analysis of data.

The largest reduction of intraocular pressure was achieved by a 6% solution of DMC (see FIG. 1-B). No further decrease in intraocular pressure was obtained with the 8% DMC solution (see FIG. 1-C). However, the magnitude of the pressure drop was dependent not only on the concentration of DMC administered, but also on the initial level of intraocular pressure at the time of the experiment. In any case, the intraocular pressure was lowered to around 25 mm Hg, a normal value of dog intraocular pressure, and no further. With regard to the duration of action, DMC action extends beyond the 6 hour period studied. The intraocular pressure of treated eyes was consistently and significantly lower than the baseline values 24 hours after drug instillation (see FIG. 1). If the data of the day 1 treatment above were plotted, the intraocular pressure at time 0 for baseline and that for treated eyes would be the same (see FIG. 2).

DMC caused only a moderate miosis. The pupil diameter decrease less than 1 mm (approximately 15%) even with the 8% concentration (see FIGS. 3-A and 3-B). In contrast, pilocarpine (4% solution) caused a marked miosis initially and leveled off gradually several days later (see FIG. 3-C).

Ocular toxicity of DMC and pilocarpine was studied with New Zealand white rabbits (1.5–2.0 kg). The eyes of all animals were examined with a slit lamp biomicroscope (Model 7451, Mentor Corp.) cobalt blue light after having been stained with fluorescein (fluor-i-strip, Ayerst Labs, Inc.). One eye of each animal was selected at random and received 25 μl of drug or buffer solution administered daily for a week. The eyes were examined at 1 and 6 hours after instillation for evidence of irritation and toxicity.

There was little evidence of conjunctival hyperemia and chemosis in the DMC treated eye even at the highest concentration (10%) studied. Such side effects were clearly evident in about half of the pilocarpine treated eyes. Examination of the DMC treated corneas under cobalt blue light after staining the fluorescein revealed that no damage to the epithelium occurred. The irises appeared normal and the aqueous humor remained clear. In all cases, the DMC treated eyes were given a rating of 0 on the scale of Draize et al. (*J. Pharmacol. Exp. Ther.* 82:377, 1944).

EXAMPLE 2

This example shows the efficacy of N-demethylated carbachol in reducing intraocular pressure in humans having open-angle glaucoma and notes the substantial absence of side effects in those treated.

Open-angle glaucoma patients were admitted to the Glaucoma Clinics at National Taiwan University Hospital. Those patients who participated in the study had discontinued all other medication two or three days earlier.

At 8:30 A.M., intraocular pressure was measured along with pupil size, blood pressure, pulse rate and occasionally, accommodation and outflow facility (tonography). Questions were also asked concerning symptoms. At 9:00 A.M., 3% DMC or 6% DMC was installed to one eye and the other eye served as control. The aforementioned measurements were repeated either every one hour or every two hours up to 8 to 12 hours. The same measurements were performed 24 and 48 hours after DMC instillation.

FIG. 4 shows the effect of 3% DMC on intraocular pressure. Three percent DMC reduced the intraocular pressure approximately 30% at the peak point. The onset was slow but duration was reasonably long. The intraocular pressure of control eyes were not affected. The diurnal effect of both eyes seemed to remain. Pupil size, pulse rate, and blood pressure were not affected. No side effects (irritation, tearing, burning, conjunctivitis, etc.), whatsoever were noted with 3% DMC.

FIG. 5 shows the result of 6% DMC instillation. Six percent DMC produced a more profound drop in intraocular pressure (approximately 36% at peak point). The diurnal effect was abolished. Interestingly, the intraocular pressure of the control eye also descreased, although to a lesser extent (30% maximum). This result indicates that DMC may be absorbed to produce its systemic effects. However, DMC is extremely weak in producing autonomic side effects. Three out of eight patients showed a slight increase in pulse rate whereas the others (five out of eight) showed a slight decrease in pulse rate. Statistically the effect was not sufficient. The same applied to the effects on the blood pressure. No side effects were noted subjectively from patient's interview or objectively from physicians' observation.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A method of reducing intraocular pressure in mammals having intraocular hypertension comprising topically administering to a hypertensive eye in an ophthalmologically acceptable, effective amount for lowering intraocular pressure of a compound selected from N,N-dimethylaminoethyl carbamate (N-demethylated carbachol) and ophthalmologically acceptable acid addition salts thereof.

2. A method according to claim 1 wherein the compound is in the form of a water-soluble ophthalmologically acceptable salt and is applied topically in an aqueous solution containing between about 3% to about 9% of said salt.

3. A method according to claim 1 wherein the compound is N,N-dimethylaminoethyl carbamate.

4. A method according to claims 1 or 2 wherein the compound is N,N-dimethylaminoethyl carbamate hydrochloride.

5. A method according to claim 1 wherein the compound is topically applied in the form of an ointment or lamella.

6. The method according to claim 1 wherein said compound is topically applied by an ophthalmologically acceptable polymeric ocular insert placed and retained in contact with the eyeball, said compound being diffusible from said insert at a rate sufficient to provide an ophthalmologically acceptable, effective intraocular pressure lowering dose thereof to the eye.

7. An ophthalmic composition for the topical treatment of open-angle glaucoma comprising in solution an intraocular pressure lowering effective amount of a water-soluble ophthalmologically aceptable acid addition salt of N,N-dimethylaminoethyl carbamate and a liquid ophthalmic carrier.

8. An ophthalmic composition according to claim 7 wherein said acid addition salt is N,N-dimethylaminoethyl carbamate hydrochloride.

9. An ophthalmic composition according to claim 8 wherein the solution comprises from about 3% to about 9% by weight N,N-dimethylaminoethyl carbamate hydrochloride.

10. A pharmaceutical unit dosage form for the topical treatment of open-angle glaucoma comprising about 4.5 mgs. to about 9.0 mgs. of N,N-dimethylaminoethyl carbamate hydrochloride in an isotonic aqueous solution.

* * * * *